United States Patent [19]
Heinze et al.

[11] Patent Number: 5,496,565
[45] Date of Patent: Mar. 5, 1996

[54] MICROSPHERULES

[75] Inventors: Friedrich Heinze, Frankfurt; Martina Clasen, Hamburg, both of Germany

[73] Assignee: Beiersdorf Aktiengesellschaft, Hamburg, Germany

[21] Appl. No.: 213,341

[22] Filed: Mar. 15, 1994

[30] Foreign Application Priority Data

Mar. 16, 1993 [DE] Germany .................. 43 08 282.3

[51] Int. Cl.⁶ .................................................. A61K 9/50
[52] U.S. Cl. .................. 424/502; 424/59; 424/401; 424/489; 514/844; 514/919; 514/938; 514/944
[58] Field of Search ..................... 424/489, 502, 424/401, 59; 514/844, 919, 938, 944

[56] References Cited

U.S. PATENT DOCUMENTS

| | | | |
|---|---|---|---|
| 4,695,452 | 9/1987 | Gannis et al. | 424/59 |
| 4,731,384 | 3/1988 | Dell et al. | 514/658 |
| 4,906,459 | 3/1990 | Cobb et al. | 424/70 |
| 5,023,089 | 6/1991 | Sakamoto et al. | 424/502 |

FOREIGN PATENT DOCUMENTS

| | | |
|---|---|---|
| 0071879 | 2/1983 | European Pat. Off. . |
| 0106173 | 4/1984 | European Pat. Off. . |
| 0346034 | 12/1989 | European Pat. Off. . |
| 0351580 | 1/1990 | European Pat. Off. . |
| 0463962 | 1/1992 | European Pat. Off. . |
| 0529396 | 3/1993 | European Pat. Off. . |
| 0535237 | 4/1993 | European Pat. Off. . |
| 2273512 | 1/1976 | France . |
| 3215211 | 10/1983 | Germany . |
| 3523454 | 1/1987 | Germany . |
| 4127665 | 2/1993 | Germany . |

OTHER PUBLICATIONS

Patents Abstracts of Japan, 61-242635 (A), Mar. 19, 1987 vol. 11, No. 89.
Patents Abstracts of Japan, 61-242634 (A), Mar. 19, 1987 vol. 11, No. 89.

*Primary Examiner*—Jyothsna Venkat
*Attorney, Agent, or Firm*—Sprung Horn Kramer & Woods

[57] ABSTRACT

Compositions of
- (a) one or more fatty alcohols selected from the group of the branched or unbranched alkyl alcohols having 16–22 C atoms,
- (b) one or more wax esters,
- (c) optionally highly disperse silica,
- (d) optionally one or more cosmetic and/or pharmaceutical active substances,
- (e) and optionally conventional pharmaceutical or cosmetic auxiliaries and/or additives.

1 Claim, No Drawings

MICROSPHERULES

The present invention relates to cosmetic and pharmaceutical matrices for the administration of cosmetic or pharmaceutical active substances. In particular, the present invention relates to matrices which are suitable for protecting active substances susceptible to chemical decomposition.

In particular, the invention relates to excipient matrices for active substances for the targeted and/or delayed release of cosmetic or pharmaceutical active substances. Furthermore, the invention relates to processes for the preparation of excipient matrices for active substances and to their use for cosmetic and pharmaceutical purposes.

Finally, the invention relates to cosmetic or pharmaceutical preparations which contain cosmetic or pharmaceutical matrices.

The invention preferably relates to topical administration.

Excipient systems for active substances for cosmetic or pharmaceutical purposes are well known per se and widely used. Examples of particulate systems are microcapsules, nanocapsules and liposomes or niosomes. The simplest excipient system for active substances is the cosmetic or pharmaceutical emulsion in which an active substance is incorporated into the dispersed phase.

A rough criterion for distinguishing between these administration forms is their size. The size of the microcapsules and the size of the dispersed emulsion droplets is in the micrometer range. The size of the nanocapsules is in the nanometer range. The sizes of liposomes and niosomes are from a few nanometers to a few micrometers. Niosomes are variants of the liposomes which are distinguished by a specific composition of the membrane.

Excipients for active substances are employed on the one hand to protect the active substance, or active substances, against environmental factors such as oxidation or light. Another purpose can be the targeted release of the active substance, or active substances, at the site of administration with the aid of the excipient system in question. For example, it is an aim to transport, with the aid of cosmetic preparations based on liposomes, active substances by diffusion through the uppermost into the deeper layers of the skin rather than leaving them to remain on the skin. The liposome wall is to dissolve in these deeper layers of the skin, and release the active substances. If the active substance were to be applied to the skin without such a system, the active substance would remain on the skin unused, or mostly unused, or it would not act in an optimal or exact fashion at the actual site of action.

Microcapsules are flowable powders or powders having particle diameters in the range of approximately 1 μm–1,000 μm. They are prepared using a range of coating processes in which finely-distributed solid, liquid and even gaseous substances are used. Polymers are conventionally used as coating or wall material. Basically, microcapsules therefore consist of two disparate zones, the core zone and the coating zone.

Preparation processes which are suitable for microencapsulation are phase separation processes (simple and complex coacervation), interface polymerization processes (polycondensation or polyaddition from dispersions) and physicomechanical processes (fluidized-bed process, spray drying).

An essential disadvantage of the conventional microencapsulation is the fact that the preparation is relatively complicated.

Microspherules are systems which are related to the microcapsules and in which there is no exact distinction between core and coating zones. However, with a size of approximately 1 μm–1,000 μm, microspherules correspond to microcapsules. In the microspherules, the embedded active substance is incorporated into the excipient matrix in solid, i.e. dispersed or dissolved form. Microspherules are therefore a specific type of microcapsules.

Cosmetic skin care is to be understood as meaning, in the first place, strengthening or repairing the natural function of the skin as a barrier against environmental factors (for example dirt, chemicals, microorganisms) and against the loss of the substances which occur in the body (for example water, natural fats, electrolytes).

If this function is disturbed, the result can be an increased resorption of toxic or allergenic substances or an attack by microorganisms and, as a consequence, toxic, irritative or allergic reactions of the skin.

Another aim of skin care is the compensation for the skin's loss of fats and water caused by daily washing. This is particularly important when the natural regeneration capacity is insufficient. Moreover, skin care products are intended to protect against environmental factors, in particular sun and wind, and to delay aging of the skin. However, this is frequently only possible by using cosmetically active substances. In this case, the development of cosmetic preparations aims at incorporating the active substances into the formulations in a stable manner and retaining their stability there over a prolonged period.

However, cosmetic active substances are frequently unstable, in particular at higher concentrations, or they are incompatible with other components of the preparations.

As a rule, medicinal topical preparations contain, as pharmaceutical active substances, one or more drugs in an effective concentration. For simplicity's sake, the legal requirements of the Federal Republic of Germany are referred to for a clear distinction between cosmetic and medicinal purposes and between the relevant products (for example Kosmetikverordnung [Cosmetics Act], Lebensmittel- und Arzneimittelgesetz [Food and Pharmaceuticals Act]).

However, the preparations of the prior art have a series of disadvantages: in many of the relevant administration forms, the chemical stabilization of many light-sensitive substances or substances which are susceptible to oxidation or hydrolysis is not guaranteed. Of course, this disadvantage is particularly grave if it is pharmaceutical active substances which are to be administered. In the case of active substances which are dissolved in emulsions, for example, Chemical reactions of the active substances or reactions of various active substances with each other or reactions of the active substances with other substances, for example auxiliaries or additives, are to be expected.

A disadvantage for cosmetic purposes is that in particular the fixation of volatile substances, for example essential oils, aroma substances or perfumes, is frequently insufficient. Conversely, cosmetic active substances frequently have characteristic or even unpleasant odours which are not acceptable in cosmetics without masking.

Even so, the disadvantage that a large number of cosmetic active substances are unstable and have to be protected against denaturation can only be remedied to a limited extent in conventional excipient systems for active substances.

Examples of substances which are unstable or to be stabilized in this sense are acetylsalicylic acid, atropine, azulene, hydrocortisone and its derivatives, for example hydrocortisone-17-valerate, vitamins, for example vitamins from the B and D series, very favourably vitamin $B_1$, vitamin $B_{12}$, vitamin $D_3$, but also the vitamins A, E, K, ascorbic acid and its derivatives, bisabolol, unsaturated fatty acids, namely the essential fatty acids (frequently also termed vitamin F,) in particular gamma-linolenic acid, oleic acid, eicosapentaenoic acid, docosahexaenoic acid and the like, furthermore natural and synthetic ceramides and ceramide-like compounds, furthermore active substances such as chloramphenicol, prostaglandins, thymol, camphor, extracts or other products of animal and vegetable origin, for example fish oils, oil of evening primrose, borage oil, blackcurrant seed oil, cod liver oil and the like.

The release characteristics of the preparations of the prior art are frequently also unsatisfactory. For example, it may happen that matrices release an active substance in a single portion, while others release the incorporated substance at such a slow rate that a cosmetic or therapeutic action is not achieved.

Compositions in which an acrylate matrix is used as a carrier matrix for eyeshadow and blusher and as absorption matrix of a skin oil absorber are known from the company brochure by Dow Corning "Offene Fragen zur Verarbeitung von Polytrap R" [Open questions on the processing of Polytrap R], in the chapter "Acrylates Copolymer: A Technique for Entrapping Cosmetic Actives" by W. L. Klein and A. J. DiSapio, Dow Corning, Montgomery, N.Y. However, these compositions have the disadvantage that the matrices crumble too readily when applied to the skin. In this manner, the desired uniform release of an active substance cannot be brought about.

DE-A 4,127,665, for example, describes galenic matrices which are compositions of (a) microcrystalline cellulose, (b) highly disperse silica, (c) at least one lipophilic component selected from the series of oils, fats and waxes and (d) if appropriate acrylate polymers and/or acrylate copolymers.

Even though the galenic matrices mentioned in this publication have outstanding cosmetic or pharmaceutical properties, their strength is that their positive characteristics are mostly shown to advantage at particle diameters of an order of magnitude of 0.5–5 mm.

This means that all known finely particulate excipient systems have at least one of the following disadvantages:

The particles are difficult to distribute, porous and, moreover, in most cases highly irregularly shaped and certainly not spherical.

The particles are frequently very large, i.e. >400 μm, and can therefore be felt on the skin as particles and cannot be applied topically in a perfect manner.

The particle size distribution is highly inhomogeneous. This means that a targeted controllability of the release of the active substance cannot be guaranteed.

The particles stabilize active substances such as, for example, unsaturated fatty acids or oil of evening primrose only insufficiently, if at all.

The particles can only be obtained on a bench scale but not on an industrial scale.

The preparation of the particles is so complicated that their use at a concentration required for an action is frequently economically not feasible.

The particles, namely true microcapsules, can only be prepared, stored or marketed in aqueous systems. This means that preservatives must always be added to such systems. However, these preservatives are frequently undesired.

The particles can only be distributed in an insufficient manner, and/or their shelf life is insufficient. This means that their properties aimed for in the end formulations cannot be achieved.

It was therefore an object of the present invention to provide compositions which do not have the disadvantages of the prior art.

In particular, it was intended to provide excipient matrices which not only have favourable release characteristics for cosmetic and pharmaceutical active substances, but which also stabilize these active substances during storage and in the end product. It is intended to prevent, inter alia, a reduction in the content of active substances upon storage, decomposition of these active substances upon storage, i.e., for example, oxidation, or the release of unpleasant odours from these active substances.

Surprisingly, it has been found, and this is how the object was achieved, that compositions of (a) one or more fatty alcohols selected from the group of the branched or unbranched alkyl alcohols having 16–22 C atoms, (b) one or more wax esters, (c) optionally highly disperse silica, (d) optionally one or more cosmetic and/or pharmaceutical active substances, (e) and optionally conventional pharmaceutical or cosmetic auxiliaries and/or additives, represent outstanding galenic matrices which overcome the problems of the prior art and are superior to the preparations of the prior art.

Examples of advantageous fatty alcohols according to the invention are cetyl alcohol, stearyl alcohol, cetyl/stearyl alcohol and behenyl alcohol.

Advantageous wax esters in the sense of the teaching on the technological procedure produced herewith are esters of higher-molecular-weight water-insoluble fatty alcohols and fatty acids. Preferred wax esters are those in which the number of the C atoms is greater than approximately 22, and preferred higher-molecular-weight fatty acids are those in which the number of the C atoms is greater than approximately 14.

Cetyl palmitate has proved particularly advantageous.

The highly disperse silica is preferably selected according to the invention from amongst the group of the ultra-pure, X-ray amorphous silica types, in particular those which can be prepared by hydrolysis of $SiCl_4$ in an oxyhydrogen flame, particularly preferably from the group of products with the commercial name Aerosil®.

Advantageous preparations relate to compositions of (a) 5–90% by weight of one or more fatty alcohols selected from the group of the branched or unbranched alkyl alcohols having 16–22 C atoms, (b) 1–90% by weight of one or more wax esters, (c) 0–20% by weight of highly disperse silica, (d) optionally containing one or more cosmetic and/or pharmaceutical active substances, (e) and conventional pharmaceutical or cosmetic auxiliaries and/or additives as desired (q.s.).

The compositions according to the invention preferably contain (a) 40–80% by weight of one or more fatty alcohols selected from the group of branched or unbranched alkyl alcohols having 16–22 C atoms, (b) 2–50% by weight of one or more wax esters, (c) 0.5–5% by weight of highly disperse silica, (d) optionally one or more cosmetic and/or pharmaceutical active substances, (e) and conventional pharmaceutical or cosmetic auxiliaries and/or additives as desired (q.s.).

The compositions according to the invention represent advantageous galenic matrices, the term "galenic matrix" being understood as meaning a solid or semi-solid substance which is used as an excipient material in cosmetics and/or pharmacy. The term includes that the matrix can be used as an excipient for active substances and, if desired, also as an adsorbent or absorbent for undesired substances which are to be eliminated.

The compositions according to the invention can be loaded with active substances by simple processes and processed to microspherules using other advantageous processes which are also fairly uncomplex.

The characteristics by which the microspherules are distinguished have been suggested at the outset. In any case, microspherules in the sense of the present invention are to be understood as meaning finely particulate systems, ideally spherical particles, in which there is no separation between core and coating zones. Rather, such microspherules are intended to represent matrix systems in which an active substance which is optionally included is incorporated in dispersed or dissolved form. It is not excluded that a plurality of series of phases can be observed in a plurality of microspherules, in particular when the active substance is in solid, dispersed form.

The size of the microspherules according to the invention is, advantageously, approximately 1 μm 1,000 μm. If desired, however, larger or smaller particle sizes can also be prepared with the compositions according to the invention. Microspherules according to the invention which are particularly suitable for topical administration are distinguished by diameters of ≦400 μm.

Thus, according to the invention, microspherules for use in cosmetic or pharmaceutical preparations are also characterized in that they are essentially composed of (a) one or more fatty alcohols selected from the group of the branched or unbranched alkyl alcohols having 16–22 C atoms, (b) one or more wax esters, (c) optionally highly disperse silica, (d) optionally one or more cosmetic and/or pharmaceutical active substances, (e) and optionally conventional pharmaceutical or cosmetic auxiliaries and/or additives.

Furthermore, cosmetic or pharmaceutical preparations, characterized in that they contain microspherules which are essentially composed of (a) one or more fatty alcohols selected from the group of the branched or unbranched alkyl alcohols having 16–22 C atoms, (b) one or more wax esters, (c) optionally highly disperse silica, (d) optionally one or more cosmetic and/or pharmaceutical active substances, (e) and optionally conventional pharmaceutical or cosmetic auxiliaries and/or additives, are considered an advantageous embodiment of the invention produced herewith.

Even though the topical use of the microspherules according to the invention is preferred, other dosage forms, for example those for parenteral nutrition or oral administration, for example in gelatine capsules, may be advantageous.

The microspherules according to the invention can be prepared in a simple manner by processes known per se. The so-called spray-drying or spray-solidification process has emerged as a particularly advantageous preparation process. The apparatuses which are customary and conventional for such processes can be used, for example those produced by NIRO ATOMIZER (Söborg, Denmark).

Thus, a process for the preparation of microspherules characterized in that a melt of (a) one or more fatty alcohols selected from the group of the branched or unbranched alkyl alcohols having 16–22 C atoms, (b) one or more wax esters, (c) optionally highly disperse silica, (d) optionally one or more cosmetic and/or pharmaceutical active substances which are in dissolved or dispersed form, (e) and optionally customary pharmaceutical or cosmetic auxiliaries and/or additives, is mechanically divided and the divided melt is solidified, is therefore considered as an advantageous process according to the invention for the preparation of microspherules according to the invention.

The mechanical division of the melt can advantageously be according to the invention that the melt is atomized by means of a nozzle, an atomizing disc or a two-substance nozzle atomizer to give microdroplets.

The final microspherules are prepared from the resulting droplets by cooling them as rapidly as possible until they solidify.

It is advantageous to carry out the cooling process in such a manner that the melt, or dispersion melt, is sprayed into a cooling gas, for example air or an inert gas. The microparticulate spray product is advantageously removed together with the stream of cooling gas, which can be maintained by means of an exhauster arranged downstream.

The fine material can be separated and discharged in cyclones. Inlet openings arranged at the ceiling of the spray tower are used for feeding cold or hot gas, it being possible to precisely control the gas with regard to temperature and quantity advantageously in such a manner that it is impossible for substantial amounts of the microspherules to settle on the external wall of the spray apparatus or the atomizer unit.

It was surprising and could not have been predicted by a person skilled in the art that the cosmetic and/or pharmaceutical compositions according to the invention would represent the basis for microspherules which are not only capable of stabilizing, in an outstanding manner, instable substances or substances which are a problem because of their odour, but which are also distinguished by outstanding release characteristics with regard to the active substance which is, or the active substances which are, incorporated.

The use of compositions of (a) one or more fatty alcohols selected from the group of the branched or unbranched alkyl alcohols having 16–22 C atoms, (b) one or more wax esters, (c) optionally highly disperse silica, (d) one or more cosmetic and/or pharmaceutical active substances which are susceptible to decomposition, (e) and optionally conventional pharmaceutical or cosmetic auxiliaries and/or additives, for stabilizing the cosmetic and/or pharmaceutical active substance, or substances, against decomposition, is also according to the invention.

The invention represents a compartmentalization of the solid/solid or solid/semi-solid or liquid/solid or liquid/semi-solid or semi-solid/semi-solid type in the pharmacotechnological sense.

After the microspherules according to the invention have been incorporated into the end formulations according to the invention (for example gels, emulsions, hydrodispersions), a stable two-phase system exists which permits the separation of chemically incompatible substances in one and the same preparation and thus creates additional stability. The immobilization of the active substance, or the active substances, achieved hereby in the compositions or microspherules according to the invention moreover reduces the risk of potential undesired reactions with substances of the surrounding liquid phase (for example in gels, emulsions, lipogels and the like).

Reactions such as, for example, the autooxidation of products which are susceptible to rancidity (unsaturated fatty acids, oil of evening primrose, Eucerit, ceramide structures), can also be contained or at least substantially delayed according to the invention.

It was thus found that substances which are susceptible, for example, against oxidative decomposition processes, are completely stable over a period which corresponds to the conventional shelf lives of ordinary cosmetics or pharmaceuticals by incorporation into the compositions according to the invention, advantageously in the form of microspherules according to the invention.

The use of microspherules which are essentially composed of
  (a) one or more fatty alcohols selected from the group of the branched or unbranched alkyl alcohols having 16–22 C atoms,
  (b) one or more wax esters,
  (c) optionally highly disperse silica,
  (d) one or more cosmetic and/or pharmaceutical active substances which are susceptible to decomposition,
  (e) and optionally conventional pharmaceutical or cosmetic auxiliaries and/or additives,
for stabilizing the cosmetic and/or pharmaceutical active substance, or substances, against decomposition, is therefore according to the invention.

It is furthermore advantageous and surprising that the galenic matrices according to the invention are obtained after the spraying/solidification process in the form of spherical or at least approximately spherical objects which can be incorporated in a trouble-free manner into conventional cosmetic or pharmaceutical bases.

The plastic character of the matrix facilitates the plasticity on the skin, which is why preparations according to the invention cause a particularly pleasant sensation.

Finally, it was surprising that compositions according to the invention in the form of microspherules according to the invention would, if desired, behave like the oil droplets of an O/W emulsion (oil-in-water-emulsion) even in water without an addition of emulsifiers.

This means that it is essentially possible to prepare emulsion-like preparations-which, in exact terms, represent dispersions of the solid/liquid or solid/semi-solid type in the sense of pharmacotechnological systems from compositions according to the invention in the form of microspherules according to the invention with water without any further additives.

However, it is also advantageous to incorporate compositions according to the invention in the form of microspherules according to the invention into conventional cosmetic or pharmaceutical preparations, for example gel, hydrodispersion or emulsion bases. Thus, it is advantageous to incorporate these microspherules into the conventional preparations of the prior art, for example into hydrophilic gels, excipient systems, lipogels, ointments, creams, simple emulsions (of the W/O and O/W types), multiple emulsions (of the W/O/W, O/W/O types and the like), mixed emulsions, hydrodispersions, suspensions and solutions.

The incorporation of the matrices according to the invention into emulsifier-free systems, i.e. in particular gels, hydrodispersions or solutions, is regarded as a particularly advantageous embodiment of the present invention.

The finely particulate microspherules present can be stored and handled in solid, dry form as an intermediate without an addition of further stabilizers such as, for example, preservatives. Their use is therefore entirely problem-free.

If the compositions of the present invention are cosmetic in nature, the following applications are particularly preferred:

Cosmetic gels, cosmetic emulsions, in particular of the O/W and W/O/W types, various types of face and bodycare preparations, peeling products, cleansing preparations, nourishing preparations, preparations which improve or repair the state of the skin, preparations containing active substances, emulsifier-free preparations, suntan preparations, insect repellents, massage gels, sports gels.

The formulation of the cosmetic bases of each of these products is known per se to a person skilled in the art.

If the preparations according to the invention are emulsions, the oil components of these emulsions can be selected from all oils, fats and waxes which are conventional in cosmetics and pharmacology, such as liquid paraffins, paraffin waxes, vegetable and animal oils, fats and waxes, for example hemp wax, flax wax, beeswax and the like, silicone oils, synthetic waxes, for example cetyl palmitate, cetyl stearate and the like, mono-, di- and triglycerides, fatty acids, fatty alcohols, montan waxes and the like.

The active substances can be selected very advantageously from the group of the lipophilic active substances, in particular from amongst the following group:

Acetylsalicylic acid, atropine, azulene, hydrocortisone and its derivatives, for example hydrocortisone- 17-valerate, vitamins, for example ascorbic acid and its derivatives, vitamins from the B and D series, very advantageously vitamin $B_1$, vitamin $B_{12}$, vitamin $D_3$, but also the vitamins A and E, in particular α-tocopherol acetate, bisabolol, unsaturated fatty acids, namely the essential fatty acids (frequently also termed vitamin F,) in particular gamma-linolenic acid, oleic acid, eicosapentaenoic acid, docosahexaenoic acid and their derivatives, chloramphenicol, caffeine, prostaglandins, thymol, camphor, extracts or other products of vegetable and animal origin, for example oil of evening primrose, borage oil, or blackcurrant seed oil, fish oils, cod liver oil, but also ceramides and ceramide-like compounds, and the like.

It is also particularly advantageous to select the active substances from amongst the group of the emollient substances, for example Eucerit and Neocerit.

Naturally, this list does not exhaust the potential of the present invention, rather, a person skilled in the art will be able to use other active substances without leaving the field of the present invention and without any inventive contribution being involved.

It is possible and advantageous according to the invention to load the compositions according to the invention, in particular the microspherules according to the invention, with a content of up to approximately 60% by weight of active substances.

It has proved to be particularly advantageous to load the compositions according to the invention, in particular the microspherules according to the invention, with a content of 0.1 up to approximately 50% by weight of active substances.

Furthermore, it is advantageous to select the content of microspherules according to the invention in cosmetic or pharmaceutical compositions according to the invention from amongst the range of 0.1–60% by weight, in particular 1–40% by weight, based on the total weight of the preparations.

As auxiliaries and additives, all substances from these substance classes which are known per se to a person skilled in the art are possible and can be used advantageously.

Preferred auxiliaries and additives are, for example, thickeners, fillers, perfume oils, colorants, active substances, such as vitamins or proteins, lipid components, in particular skin-related lipids or those lipids which resemble the skin's lipids, separating agents, pharmaceutical active substances, light stabilizers, stabilizers, such as UV stabilizers, insect repellents, alcohol, water, salts, proteolytically or keratolytically active substances, and the like.

If desired, emulsifiers can also be used in advantageous embodiments of the present inventions.

It is possible and advantageous according to the invention to dispense with preservatives and antioxidants. If appropriate, the use of these substances as auxiliaries or additives may, however, be advantageous.

Furthermore, it is advantageous to incorporate the compositions according to the invention into the end formulations by means of the mixing systems conventionally used in emulsion technology.

The present invention allows lipophilic auxiliaries and active substances to be retained in the galenic matrix and, in particular if the matrix is in the form of microspherules according to the invention, in the preparation in question, without the use of emulsifiers, for example when the system around the microspherules is a gel or a solution. This allows the skin-irritant and/or allergenic potential of this substance class to be avoided in these systems. Hydrodispersions, which represent systems of the solid/liquid type, have proved to be advantageous embodiments of emulsifier-free preparations according to the invention.

The particulate distribution state in the preparations allows a reduction of the reactive surface area of the active substance, or active substances, to be achieved. Compartmentalization reduces the reactivity of the active substances greatly.

Even active substances which are highly problematic with regard to odour can be processed according to the invention in high concentrations without the tolerability of the preparation according to the invention with regard to odour suffering.

The final cosmetic and pharmaceutical preparations, too, are distinguished by a highly advantageous action. Not only are the incorporated active substances as well as the preparations themselves highly stable, but in particular a high capacity for the controlled and targeted release of active substance following topical administration can be found.

For example, it has been shown that the release characteristics with regard to the release rate and completeness of the release of active substance in cosmetic or pharmaceutical preparations which contain active-substance-containing microspherules according to the invention do not differ significantly from those preparations which contain the same active substance in a cosmetic or pharmaceutical preparation, but without a surrounding matrix. This was found in vitro in a permeation test on prepared pigskin. In the preparations according to the invention themselves, the active substance, or the active substances, in particular caffeine and α-tocopherol acetate, do not diffuse out of the matrices, or microspherules, into the surrounding medium.

It would have been expected that matrix systems release a given active substance more slowly, or incompletely.

Furthermore, it was possible to check the stabilizing action of the preparations according to the invention in particular of the microspherules according to the invention, with the aid of measurements in the Ranzimat Test (by Metrohm): after temperature stress, for example, the oil of evening primrose, which is susceptible to oxidation, was destroyed after a considerably longer incubation time than in those conventional formulations of the prior art, even in comparison with those in which the oil of evening primrose was either in microencapsulated form or protected by antioxidants. The same applies to ceramides and ceramide-like compounds.

The examples which follow are intended to illustrate the nature of the present invention without intentionally restricting the invention to these examples. Rather, a person skilled in the art can carry out a wide range of variations based on his general expert knowledge, but these variations will not exceed the scope of the present invention. The quantities in the formulations or examples are % by weight, unless expressly indicated otherwise.

| Formulation I | |
|---|---|
| | % by weight |
| Active substance I (oil of evening primrose) | 25.00 |
| Active substance II (Eucerit) | 2.50 |
| Active substance III (ceramide HO 3, from Rahn/Sederma) | 3.00 |
| Behenyl alcohol | 52.00 |
| Cetyl palmitate | 8.50 |
| Ascorbyl palmitate | q.s. |
| Highly disperse SiO$_2$ | 7.50 |

The formulation is heated at approximately 40°–50° C., taking the form of a dispersion melt. This melt is homogenized by vigorous stirring and transferred directly from the temperature-controlled vessel into a NIRO-ATOMIZER apparatus for NIRO P7.

| Apparatus parameters: | |
|---|---|
| Atomizer unit | Disc D, 14,000 rpm |
| Feed air temperature | 9° C. |
| Exhaust air temperature | 12° C. |
| Air flow rate | 400 m$^3$/h |
| Product flow rate | 15.5 kg/h, Watson-Marlow pump 502S, pump capacity 25% |

Microspherules in the size range of approximately 10–450 μm are obtained in a yield of >90%.

| Formulation II | |
|---|---|
| | % by weight |
| Oil of evening primrose | 25.00 |
| Behenyl alcohol | 66.00 |
| Cetyl palmitate | 7.50 |
| Propyl gallate | 0.02 |
| Highly disperse SiO$_2$ | 1.98 |

The formulation is heated at approximately 40°–50° C., taking the form of a clear melt. This melt is homogenized by vigorous stirring and transferred directly from the temperature-controlled vessel into a NIRO-ATOMIZER apparatus for NIRO P7.

| Apparatus parameters: | |
|---|---|
| Atomizer unit | Disc D, 14,000 rpm |
| Feed air temperature | 12° C. |
| Exhaust air temperature | 21° C. |
| Air flow rate | 400 m³/h |
| Product flow rate | 15.5 kg/h, Watson-Marlow pump 502S, pump capacity 25% |

Microspherules in the size range of approximately 10–450 µm are obtained in a yield of >90%.

| Formulation III | |
|---|---|
| | % by weight |
| α-Tocopheryl acetate | 30.00 |
| Behenyl alcohol | 65.00 |
| Cetyl palmitate | 3.50 |
| Ascorbyl palmitate | 0.50 |
| Highly disperse SiO₂ | 1.00 |

The formulation is heated at approximately 40°–50° C., taking the form of a clear melt. This melt is homogenized by vigorous stirring and transferred directly from the temperature-controlled vessel into a NIRO-ATOMIZER apparatus for NIRO P7.

| Apparatus parameters: | |
|---|---|
| Atomizer unit | Disc D, 14,000 rpm |
| Feed air temperature | 11° C. |
| Exhaust air temperature | 18° C. |
| Air flow rate | 400 m³/h |
| Product flow rate | 15.5 kg/h, Watson-Marlow pump 502S, pump capacity 25% |

Microspherules in the size range of approximately 10–450 µm are obtained in a yield of >95%.

| Formulation IV | |
|---|---|
| | % by weight |
| Ceramide HO 3 ® | 3.50 |
| Eucerit ® | 2.50 |
| Oil of evening primrose | 25.00 |
| Behenyl alcohol | 63.50 |
| Cetyl palmitate | 4.50 |
| Ascorbyl palmitate | 0.50 |
| Highly disperse SiO₂ | 0.50 |

The formulation is heated at approximately 40°–50° C., taking the form of a clear melt. This melt is homogenized by vigorous stirring and transferred directly from the temperature-controlled vessel into a NIRO-ATOMIZER apparatus for NIRO P7.

| Apparatus parameters: | |
|---|---|
| Atomizer unit | Disc D, 14,000 rpm |
| Feed air temperature | 9° C. |
| Exhaust air temperature | 12° C. |
| Air flow rate | 400 m³/h |
| Product flow rate | 15.5 kg/h, Watson-Marlow pump 502S, pump capacity 25 |

Microspherules in the size range of approximately 10–450 µm are obtained in a yield of >90%.

| Formulation V | |
|---|---|
| | % by weight |
| Caffeine | 1.50 |
| Cetyl stearyl alcohol | 21.00 |
| Cetyl palmitate | 76.50 |
| Highly disperse SiO₂ | 1.50 |

The formulation is heated at approximately 40°–50° C., taking the form of a dispersion melt. This melt is homogenized by vigorous stirring and transferred directly from the temperature-controlled vessel into a NIRO-ATOMIZER apparatus for NIRO P7.

| Apparatus parameters: | |
|---|---|
| Atomizer unit | Disc D, 14,000 rpm |
| Feed air temperature | 9° C. |
| Exhaust air temperature | 12° C. |
| Air flow rate | 400 m³/h |
| Product flow rate | 15.5 kg/h, Watson-Marlow pump 502S, pump capacity 25% |

Microspherules in the size range of approximately 10–450 µm are obtained in a yield of >90%.

In the examples which follow, the microspherules are in accordance with formulations I–V.

EXAMPLE 1

| Aqueous preparation (face tonic) | |
|---|---|
| | % by weight |
| PEG-40-hydrogenated castor oil | 0.811 |
| Dipropylene glycol | 2.534 |
| PEG-8 | 1.521 |
| Na₃EDTA | 0.253 |
| Polymer JR 125 | 0.025 |
| Formulation I | 0.750 |
| Fully demineralized water | to 100.000 |

EXAMPLE 2

| Aqueous composition | |
|---|---|
| | % by weight |
| Poly fatty acid ester (Cetiol HE) | 16.000 |
| PPG 3-myristyl ether (Witconol APM) | 1.000 |
| Propylene glycol | 3.000 |
| Glycerol | 40.000 |
| Formulation II | 0.500 |
| Fully demineralized water | to 100.000 |

EXAMPLE 3

Hydrogel (polyacrylate gel)

| | % by weight |
|---|---|
| Acrylic acid polymerizate (Carbopol 981) | 1.000 |
| Tris(hydroxymethylamino)methane (Tris) | 1.000 |
| Glycerol | 2.000 |
| Propylene glycol | 2.000 |
| Formulation III | 12.500 |
| Fully demineralized water | to 100.000 |

EXAMPLE 4

High water-containing emulsion (very soft)

| | % by weight |
|---|---|
| Ceteareth (Cremophor A 25) | 0.100 |
| Cetearyl alcohol (Lanette 0) | 0.400 |
| White petroleum jelly, DAB 9 | 12.500 |
| Mineral oil, DAB 9 | 11.000 |
| Ceteareth-6-stearyl alcohol (Cremophor A6) | 6.000 |
| Formulation IV | 11.000 |
| Fully demineralized water | to 100.000 |

EXAMPLE 5

High water-containing emulsion

| | % by weight |
|---|---|
| Ceteareth-25 (Cremophor A25) | 1.500 |
| Cetearyl alcohol (Lanette 0) | 8.500 |
| Formulation V | 8.000 |
| Fully demineralized water | to 100.000 |

EXAMPLE 6

High water-containing emulsion

| | % by weight |
|---|---|
| Ceteareth-25 (Cremophor A25) | 2.000 |
| Cetearyl alcohol (Lanette 0) | 8.000 |
| White petroleum jelly, DAB 9 | 10.000 |
| Mineral oil, DAB 9 | 10.000 |
| Formulation I | 10.000 |
| Fully demineralized water | to 100.000 |

EXAMPLE 7

O/W emulsion

| | % by weight |
|---|---|
| PEG-100-stearate (Arlacel 165) | 5.000 |
| Cetearyl alcohol (Lanette 0) | 3.000 |
| Mineral oil, DAB 9 | 25.000 |
| Paraben mixture | as desired |
| Formulation III | 7.300 |
| Fully demineralized water | to 100.000 |

EXAMPLE 8

O/W emulsion

| | % by weight |
|---|---|
| Polysorbate-60 (Tween 60) | 3.000 |
| Sorbitan stearate (Arlacel 60) | 2.000 |
| Cetearyl alcohol (Lanette 0) | 3.000 |
| Mineral oil, DAB 9 | 25.000 |
| Paraben mixture | as desired |
| Formulation IV | 0.035 |
| Fully demineralized water | to 100.000 |

EXAMPLE 9

Ionic O/W emulsion

| | % by weight |
|---|---|
| Stearic acid | 5.000 |
| Cetearyl alcohol (Lanette 0) | 3.000 |
| Mineral oil, DAB 9 | 25.000 |
| Paraben mixture | as desired |
| Triethanolamine | 1.000 |
| Formulation IV | 17.000 |
| Fully demineralized water | to 100.000 |

EXAMPLE 10

Hydrodispersion gel with UV filter

| | % by weight |
|---|---|
| Formulation III | 7.500 |
| 2-Phenylbenzimidazole-5-sulphonic acid ("Eusolex 232", Merck) | 0.800 |
| Allantoin | 2.000 |
| Liquid sorbitol ("Karion F", Merck) | 2.000 |
| "Carbopol 934", B.F. Goodrich | 1.500 |
| Tris(hydroxymethyl)aminomethane | 2.700 |
| Propylene glycol | 1.000 |
| Ethanol | 10.000 |
| Perfume, improvers, additives, antioxidants, stabilizers | q.s. |
| Water | to 100.000 |

EXAMPLE 11

Day cream (O/W emulsion) with UV filters

| | % by weight |
|---|---|
| Formulation III | 2.500 |
| PEG-5 glyceryl stearate | 2.000 |
| Silicone oil | 1.500 |
| Eucerit ® | 0.500 |
| Isopropyl palmitate | 2.000 |
| $C_{12}$ – $C_{15}$ alkyl benzoate | 2.000 |
| Octyldodecanol | 1.000 |
| Butylene glycol | 2.000 |
| Cetyl alcohol | 3.000 |
| Octyl methoxycinnamate | 0.500 |
| $TiO_2$ | 0.200 |
| Fully demineralized water | to 100.000 |

The preparation is buffered to pH 5 using a citrate buffer.

EXAMPLE 12

Light night cream (O/W emulsion)

| | % by weight |
|---|---|
| Formulation II | 7.000 |
| Hydrogenated coconut fatty acid glycerides | 5.000 |
| Octyldodecanol | 4.000 |
| Eucerit ® | 0.500 |
| Silicone oil | 1.000 |
| $C_{12} - C_{15}$ alkyl benzoate | 4.000 |
| PEG-5 glyceryl stearate | 1.500 |
| PEG-5 stearyl stearate | 1.500 |
| Squalane | 0.500 |
| Cetyl alcohol | 2.000 |
| Carbopol 934 | 0.200 |
| Shea butter | 2.000 |
| Bisabolol | 0.800 |
| Allantoin | 0.200 |
| Sodium hyaluronate | 0.100 |
| Panthenol | 1.000 |
| Fully demineralized water | to 100.000 |

The preparation is buffered to pH 5 using a citrate buffer.

EXAMPLE 13

| | % by weight |
|---|---|
| Formulation IV | 6.500 |
| Caprylic acid/capric acid triglyceride | 2.500 |
| Liquid paraffin DAB 9 | 3.500 |
| Simethicone | 0.200 |
| Isopropyl palmitate | 1.500 |
| Glycerol | 3.000 |
| Butylene glycol | 1.500 |
| Polyethylene glycol 150 | 2.000 |
| Acrylate/$C_{10} - C_{30}$ alkyl acrylate copolymer | 0.400 |
| Mg/Al silicate | 0.400 |
| Polyvinylpyrrolidone | 0.500 |
| $ZnSO_4$ | 0.400 |
| NaOH | 0.400 |
| Ethanol | 1.000 |
| Fully demineralized water | to 100.000 |

The preparation is buffered to pH 5 using a citrate buffer.

We claim:

1. Microspherules of a composition by weight consisting essentially of
   (a) 1–20% if at least one fatty alcohol having 16–22 C atoms and selected from the group consisting of cetyl alcohol, stearyl alcohol and behenyl alcohol,
   (b) 1–20% cetyl palmitate,
   (c) 1–20% of highly disperse silica, and
   (d) optionally at least one cosmetically or pharmaceutically active substance, auxiliary or additive.

* * * * *